United States Patent [19]
Budolfsen et al.

[11] Patent Number: 5,998,176
[45] Date of Patent: Dec. 7, 1999

[54] GELLING OF PECTIC MATERIAL USING CARBOXYLIC ESTER HYDROLASE AND OXIDASE AND/OR PEROXIDASE

[75] Inventors: Gitte Budolfsen, Frederiksberg; Lars Saaby Pedersen, Farum, both of Denmark

[73] Assignee: Novo Nordisk A/S, Bagsvaerd, Denmark

[21] Appl. No.: 09/085,344

[22] Filed: May 27, 1998

Related U.S. Application Data

[63] Continuation of application No. PCT/DK97/00037, Jan. 27, 1997.

[30] Foreign Application Priority Data

Jan. 26, 1996 [DK] Denmark .................................. 0092/96

[51] Int. Cl.$^6$ .............................. C12P 19/04; C12P 19/00

[52] U.S. Cl. .............................................. 435/101; 435/72

[58] Field of Search ........................................ 435/101, 72

[56] References Cited

U.S. PATENT DOCUMENTS

| | | | |
|---|---|---|---|
| 4,672,034 | 6/1987 | Rombouts | 435/101 |
| 5,443,975 | 8/1995 | Cervelli et al. | 435/175 |

FOREIGN PATENT DOCUMENTS

| | | |
|---|---|---|
| WO 94/12055 | 6/1994 | WIPO . |
| WO 94/25575 | 11/1994 | WIPO . |
| WO 96/03440 | 2/1996 | WIPO . |

OTHER PUBLICATIONS

Milstein et al., "Transformation of lignin–related compounds with laccase in organic solvents", Journal of Biotechnology, 1993, vol. 30, pp. 37–47.

Rombouts et al., Enzymatic and chemical degradation and the fine structure of pectins from sugar–beet pulp, Carbohydrate Research, 1986, vol. 154, pp. 189–203.

Williamson et al., "Gelation of sugarbeet and citrus pectins using enzymes extracted from orange peel", Carbohydra. Polym., 1990, 13(4), pp. 387–397.

Guillon et al., "Oxidative cross–linking of chemically and enzymatically modified sugar–beet pectin", Carbohydr. Polym., 1990, 12(4), pp. 352–374.

*Primary Examiner*—Sandra E. Saucier
*Assistant Examiner*—Vera Afremova
*Attorney, Agent, or Firm*—Steve T. Zelson, Esq.; Reza Green, Esq.

[57] ABSTRACT

A method for causing gelling or increase of viscosity of an aqueous medium containing a gellable polymeric material which has functionalities with phenolic hydroxy groups, and which, in aqueous medium, is susceptible to viscosity increase or gelling in the presence of a carboxylic ester hydrolase, comprises treating the aqueous medium with: a carboxylic ester hydrolase (EC 3.1.1); and an oxidase (EC 1.10.3) and/or a peroxidase (EC 1.11.1); in the presence of an oxidizing agent suitable for use with the oxidase and/or peroxidase. Gelled products obtainable by the method may be dried or dehydrated to give products which are useful as absorbents for absorbing aqueous media, such as body fluids. In particular, gelling a pectic material obtainable from sugar beets using pectinesterase (EC 3.1.1.11) and laccase (EC 1.10.3.2).

16 Claims, No Drawings

GELLING OF PECTIC MATERIAL USING CARBOXYLIC ESTER HYDROLASE AND OXIDASE AND/OR PEROXIDASE

CROSS-REFERENCE TO RELATED APPLICATIONS

This application is a continuation of PCT/DK97/00037 filed on Jan. 27, 1997 and claims priority under 35 U.S.C. 119 of Danish application serial no. 0092/96 filed Jan. 26, 1996, the contents of which are fully incorporated herein by reference.

FIELD OF THE INVENTION

The present invention relates to a method for causing gelling (gelation) or increase of viscosity of aqueous media containing gellable polymeric materials, notably pectins or pectic materials, which have functionalities or substituents with phenolic hydroxy groups and which, in aqueous medium, are susceptible to viscosity increase or gelling in the presence of certain carboxylic ester hydrolases, especially pectinesterases (vide infra).

BACKGROUND OF THE INVENTION

The use of a type of enzyme known as a "pectinesterase" (EC 3.1.1.11; systematic name "pectin pectylhydrolase"; also known as "pectin esterase", "pectin methylesterase", "pectin methoxylase" or "pectin demethoxylase"; abbreviated hereafter as PE) for causing gelling or increase of viscosity of aqueous media containing certain pectins is well known. By way of example, WO 94/12055 (Gist-Brocades N.V.) and WO 94/25575 (Novo Nordisk A/S) both describe, inter alia, foodstuff-related applications of PE-catalyzed gelling or viscosity increase of pectin-containing media.

Moreover, certain pectins (hereafter often referred to as "phenolic pectins"), notably pectins obtainable from members of the plant family Chenopodiaceae (which includes beets and spinach), as well as hemicellulosic material from some cereals (e.g. from wheat and maize), are substituted to some extent with substituents derived from certain carboxylic acids containing phenolic hydroxy groups. These phenolic substituents are often derived from substituted cinnamic acids, and in the case of, e.g., phenolic pectins the substituents in question are often "ferulyl" functionalities, i.e. ester functionalities derived from "ferulic acid" (4-hydroxy-3-methoxycinnamic acid; it does ot appear to have been established clearly whether "ferulic acid" embraces cis or trans isomeric forms, or both).

With respect to the gelling or increase of viscosity of aqueous media containing such phenolic pectins (and some related phenolic polysaccharides) by processes which do not involve the use of PE, the following may be mentioned:

J.-F. Thibault et al., in *The Chemistry and Technology of Pectin*, Academic Press 1991, Chapter 7, pp. 119–133, describe the oxidative cross-linking of beet pectins (in connection with the gelling thereof) by purely chemical modification, using a powerful oxidant such as, e.g, persulfate. With respect to enzyme-catalyzed processes, the Thibault et al. reference also describes the gelling of sugar beet pectin using a combination of a peroxidase and hydrogen peroxide.

FR 2 545 101 A1 describes a process for modification (including gelling) of beet pectin involving the use of "an oxidizing system comprising at least an oxidizing agent and an enzyme for which the oxidizing agent in question is a substrate". The only types of oxidizing agent and enzyme which are specified and/or for which working examples are given are hydrogen peroxide and peroxidases, respectively.

Similarly, WO 93/10158 describes gelling of aqueous hemicellulosic material containing phenolic substituents [e.g. substituents derived from ferulic acid (vide supra)] using an oxidizing system comprising a peroxide (such as hydrogen peroxide) and an "oxygenase" (preferably a peroxidase).

Applicant's co-pending PCT application No. PCT/DK95/00317 (unpublished at the time of filing of the present application) discloses a method for causing gelling or increase of viscosity of an aqueous medium containing a gellable polymeric material having substituents with phenolic hydroxy groups (such as a phenolic pectin as mentioned above), the method comprising adding an oxidase to the aqueous medium. The oxidase enzymes in question (which are generally classified under EC 1.10.3) are oxidoreductases (EC 1) which are capable of catalyzing oxidation of phenolic groups and which employ molecular oxygen as acceptor. Preferred oxidases in the context of the invention disclosed in PCT/DK95/00317 are laccases (EC 1.10.3.2).

Phenolic pectins of the above-mentioned types, which are preferred starting materials in the context of the present invention, and which—as already mentioned—are naturally occurring phenolic polysaccharides, are readily available relatively cheaply and are of proven physiological safety with regard to ingestion by, and contact with, humans and animals.

SUMMARY OF THE INVENTION

It has now surprisingly been found that substances (such as phenolic pectins) which (i) have functionalities or substituents with phenolic hydroxy groups, and (ii) are susceptible, in aqueous medium, to gelling or viscosity increase in the presence of certain carboxylic ester hydrolases (such as pectinesterases), can undergo improved gelling or viscosity increase when subjected to treatment not only with such a carboxylic acid esterase, but also with an oxidase (notably an oxidase classified under EC 1.10.3) and/or a peroxidase (EC 1.11.1; such as a peroxidase classified under EC 1.11.1.7), in the presence of an appropriate oxidizing agent [i.e. an oxidizing agent which is suitable for use with the oxidase and/or peroxidase in question, preferably one which is satisfactorily compatible with other components (such as gellable starting material, or other enzymes present) present in the reaction medium, i.e. an oxidizing agent whose use in the process of the invention does not lead to adverse effects on such components].

Areas of application of the resulting gelled or viscous products include, but—as disclosed below (vide infra)—are by no means limited to, the following:

Foodstuff applications: as a thickening and/or stabilising agent in sauces, gravy, desserts, toppings, ice cream and the like; as a setting agent in marmelades, jams, gellies and the like; as a viscosity-regulating agent in flavouring extracts and the like.

Medical/medicinal applications: as a material for drug encapsulation; as a slow release vehicle for drug delivery (e.g. oral, anal or vaginal); as a material for a wound or burn dressing.

Agricultural/horticultural applications: as a slow release vehicle for pesticide delivery (i.e. as a biocontainer); as a plant culture medium.

DETAILED DESCRIPTION OF THE INVENTION

The present invention relates to a method for causing gelling or increase of viscosity of an aqueous medium containing a gellable material, normally a gellable polymeric material, such as a pectin or other pectic material, which has functionalities or substituents with phenolic hydroxy groups and which, in aqueous medium, is susceptible to viscosity increase or gelling in the presence of a carboxylic ester hydrolase, especially a pectinesterase (vide infra). The method of the invention comprises treating the aqueous medium with: a carboxylic ester hydrolase [preferably a pectinesterase (PE), EC 3.1.1.11]; and an oxidase (preferably a laccase, EC 1.10.3.2) and/or a peroxidase (preferably a peroxidase classified under EC 1.11.1.7); in the presence of an oxidizing agent suitable for use with the oxidase and/or peroxidase.

With respect to the order of addition of the enzymes in question to the aqueous medium, it is generally preferable either to add the carboxylic ester hydrolase to the medium before adding the oxidase and/or peroxidase, or to introduce the various enzymes substantially simultaneously into the medium.

Gel Formation

Gel formation promoted by treatment with carboxylic ester hydrolases: Without being bound to any particular theory, gel formation or viscosity increase following addition of a carboxylic ester hydrolase (such as a pectinesterase), in the absence of addition of an oxidase enzyme, to an aqueous medium containing a gellable material of the type in question (e.g. a pectic material) is believed to result primarily from the formation of a three-dimensional network of predominantly electrostatic interactions (ionic bonds) between divalent metal ions, notably $Ca^{2+}$ ions, and carboxylate (i.e. —$COO^-$) functionalities, at least some of which are present as a result of hydrolase-catalyzed hydrolysis of ester bonds (primarily methyl ester bonds in the case of a pectic material; vide infra).

Gel formation or viscosity increase in this manner will thus generally require that the aqueous medium to which the carboxylic ester hydrolase is added contains an adequate concentration of appropriate metal ions (very suitably calcium ions), and this may, if the initial concentration of such ions in the medium is too low, require that appropriate metal ions be added to the medium.

Gel formation promoted by treatment with oxidases and/or peroxidases: Without being bound to any particular theory, gel formation or viscosity increase following addition of an oxidase and/or a peroxidase (in the absence of addition of a carboxylic ester hydrolase) to an aqueous medium containing a relevant type of phenolic polymer (e.g. a phenolic pectin), in the presence of an appropriate oxidizing agent, is believed to result from polymerization via cross-linking between the phenolic groups of the material in question, presumably via the formation of phenoxy radicals from the hydroxylated aromatic substituents. Increasing cross-linking in this manner is believed to lead to the formation of an extended, three-dimensionally cross-linked structure, with attendant gelling.

Gel strength: It is well known that the physical properties of gels differ greatly from those of corresponding non-gelled solutions. The physical properties of gelled products, and the properties conferred on a product by inclusion of a gel therein, may be characterized by a variety of techniques.

In one such technique, which is known as "Texture Analysis" and which is employed in the working examples herein (vide infra), the "strength" or hardness of a gel is measured by compressing the gel to a chosen extent (such as 20–30%) and at a chosen rate and recording the applied force as a function of, e.g., time. The gel strength [which is normally given in Newtons per square meter ($N/m^2$)] is then determined as the peak force on the force-time curve.

Gellable materials

As already indicated above, gellable materials suitable for use in the method of the invention will, in general, be polymeric materials.

Useful gellable polymeric materials include certain types of polysaccharide-based polymers, a number of which are readily obtainable from natural sources (primarily from plants) and are particularly well suited when the product formed according to the method is to be employed, for example, in the manufacture of a foodstuff for human and/or animal ingestion, or in the manufacture of a medicinal, therapeutic or other product for ingestion by, or external application to, humans or animals. Moreover, as a consequence of their ready biological renewability and degradability, such polymeric materials of natural origin are, in general, highly environmentally friendly.

Pectins constitute a particularly interesting class of such substances. As already mentioned, pectins obtainable from members of the plant family Chenopodiaceae (which includes sugar beets, mangelwurzels, beetroot, leaf beets, spinach and quinoa) contain phenolic substituents derived from cinnamic acid. Pectins are made up of "smooth" regions, based on linear homogalacturonan, and "hairy" (ramified) regions, based on a rhamnogalacturonan backbone with side-branches of varying length.

The linear homogalacturonan part of pectins is based on chains of 1,4-linked α-D-galacturonic acid, and this polygalacturonic acid is esterified with methyl groups (also termed "methoxylated") to varying degrees—depending on the plant species in question—and may (as in, e.g., sugar beet pectin) further be partially acetylated. In this connection, pectins are sometimes classified as "high-methoxy" pectins (normally defined as those in which the degree of methyl esterification of the polygalacturonic acid is greater than about 50%) or "low-methoxy" pectins (normally defined as those in which the degree of methyl esterification of the polygalacturonic acid is about 50% or less).

As mentioned above, gelling or viscosity increase in, e.g., pectin-based aqueous media can take place as a result of formation of a three-dimensional network of ionic bonds between carboxylate anions and, e.g., $Ca^{2+}$ ions. It is appropriate to mention here that certain pectins, notably low-methoxy pectins with a relatively high intrinsic content of unesterified carboxylate functionalities, can undergo gelling or viscosity increase to some extent in aqueous medium in the presence of, e.g., calcium ions without any treatment with a pectinesterase or other carboxylic ester hydrolase.

When employing a pectic material (e.g. sugar beet pectin or a related phenolic pectin) as gellable material in the process of the invention, the aqueous medium in question will preferably contain divalent metal ions (such as $Ca^{2+}$, $Mg^{2+}$ or $Fe^{2+}$) in an amount in the range of 0.1–100 mg per gram (dry weight) of pectic material, more preferably 0.5–50 mg per gram (dry weight), such as 1–30 mg per gram (dry weight) of pectic material. Calcium ions ($Ca^{2+}$) are preferred.

Rhamnogalacturonans are polysaccharides with more or less regularly alternating rhamnose and galacturonic acid residues in the backbone. The rhamnogalacturonan backbone in the hairy regions of pectins have acetyl groups on the galacturonic acid residues [cf. H. A. Schols in Carbohydr. Res. 206 (1990), pp. 117–129]; the side-branches include oligo- and polysaccharides such as arabinan and arabinogalactan, which are linked to the rhamnose in the rhamnogalacturonan backbone.

Sugar beet pectin is especially rich in arabinan. Arabinan contains β-1,5-linked arabinose in the backbone with α-(1–

>3)- or α-(1->2)-linked arabinose residues, whereas arabinogalactan contains β-1,4-linked galactose in the backbone, with α-(1->3) or α-(1->2) linked arabinose residues. Ferulyl substituents are linked to the arabinose and/or the galactose in the arabinan and arabinogalactan side-branches of the rhamnogalacturonan part. The "ferulic acid" (ferulyl) content in sugar beet pectin depends upon the method of extraction, but is often about 0.6% [cf. F. Guillon and J.-F. Thibault, *Carbohydrate Polymers* 12 (1990) 353–374].

It is known that beet pectin obtained by a process which results in partial removal of the arabinose residues which are present in beet pectin in the form in which it occurs in, e.g., beet pulp may exhibit improved gelling properties. Thus, e.g., procedures involving a mild acid treatment and/or a treatment with an α-arabinofuranosidase will improve the gelling properties of the pectin [F. Guillon and J.-F. Thibault (vide supra)]. As described and illustrated below, a treatment of this kind may also be employed in certain embodiments of the method of the present invention.

Phenolic pectic materials (i.e. phenolic pectins or modified phenolic pectins) of the above-mentioned types—notably pectins obtainable from members of the plant family Chenopodiaceae, such as sugar beet pectins—are among the preferred types of phenolic polymers in the context of the invention.

The phenolic-substituted cinnamic acid ester (ferulic acid ester) linkages in phenolic pectins can be hydrolyzed by ferulic acid esterases. Enzymes used in the purification of, e.g., polysaccharides containing substituents of the cinnamic acid type should therefore be essentially free from ferulic acid esterase activity with specificity towards ferulic acid esters of the polysaccharide in question. Under conditions of low water activity, ferulic acid esterase will catalyse the formation of new ester linkages to hydroxyl groups in carbohydrates, and can therefore be used to increase the content of ester residues of the phenolic cinnamic acid ester type (e.g. ferulyl residues) in pectins (including pectin from beet, or from other members of the plant family Chenopodiaceae) and thereby improve their gelling properties in the context of the invention.

Thus, under conditions of low water activity, ferulic acid esterases may be used to attach groups of the cinnamic acid ester type (e.g. ferulic acid ester groups) to pectins (and possibly other types of, e.g., hydroxylic polymers which are susceptible to viscosity increase or gelling in the presence of a carboxylic ester hydrolase, such as a pectinesterase) which do not contain phenolic residues useful for achieving gelation, and thereby render them susceptible to oxidase- and/or peroxidase-catalyzed gelation.

Ester linkages to phenolic cinnamic acids (or other phenolic carboxylic acids) may also be synthesized by non-enzymatic methods known in the art. Polymers which contain acid groups, such as pectins, can be esterified with polyhydric phenolic substances, e.g. ferulic alcohol, sinapyl alcohol or lignin derivatives, in order to obtain a phenolic polymer with the ability to undergo oxidative gelation.

Particularly interesting phenolic substituents in the context of the present invention include those comprising one or two methoxy groups in an ortho-position in the aromatic ring relative to the phenolic hydroxy group [as in the case of, e.g., ferulyl (4-hydroxy-3-methoxycinnamyl) substituents].

The concentration of phenolic polymer (e.g. a phenolic pectic material) present in the aqueous medium employed in the process of the invention will normally be in the range of 0.1–10% by weight of the medium, for example in the range of 0.5–5% by weight. Concentrations of phenolic polymer in the range of about 1–5% by weight will often be appropriate.

Enzymes

Enzyme classification numbers (EC numbers) referred to in the present specification with claims are in accordance with the *Recommendations* (1992) *of the Nomenclature Committee of the International Union of Biochemistry and Molecular Biology,* Academic Press Inc., 1992.

Carboxylic ester hydrolases: As already indicated, preferred carboxylic ester hydrolases (EC 3.1.1) in the context of the present invention are pectinesterases (EC 3.1.1.11). Other carboxylic ester hydrolases of possible relevance include carboxylesterases (EC 3.1.1.1).

Pectinesterases suitable for use in the process of the invention are obtainable, for example, from a variety of plant and microbial sources. Preferred pectinesterases include those obtainable from a fungus, such as a fungus of the genus Aspergillus, e.g. pectinesterase obtainable from *A. japonicus* (S. Ishii et al., *Journal of Food Science* 44 (1979), pp. 611–614), *A. aculeatus, A. niger* (EP 0 388 593 A1) or *A. awamori* (EP 0 388 593 A1), or a fungus of the genera Fusarium, Sclerotonia or Penicillium (DE 2843351; U.S. Pat. No. 4,200,694). Such fungal pectinesterases exhibit a relatively low pH optimum and are well suited for use in the context of the present invention.

When, for example, a pectic material is employed as gellable material in the process of the invention, the amount of pectinesterase employed in the process should normally be in the range of 0.1–100 PEU per kilogram (dry weight) of pectic material, preferably 1–100 PEU/kg, such as 10–100 PEU/kg.

Determination of pectinesterase activity (PEU)

1 PEU corresponds to an amount of pectinesterase which causes hydrolysis of 1 mmol of pectin methyl ester per minute with citrus pectin (72% methyl esterification) substrate at 0.5% by weight (% w/w) substrate concentration, pH 4.8. Further details concerning the analytical method are given in a brochure, ABT-SM-0005.1.01/Drf5.3, available on request from Novo Nordisk A/S, Bagsvaerd, Denmark.

Pectinesterase preparations employed in the context of the present invention are preferably substantially free of any pectin depolymerase activity (i.e. substantially free of any enzyme—such as a "pectate lyase", "pectin lyase" or "polygalacturonase"—which catalyzes depolymerization of the polysaccharide backbone of pectin). Such pectinesterases are obtainable by using a host system for the expression of the enzyme which produces substantially no pectin-depolymerizing enzymes (see, e.g., WO 94/25575).

Oxidases: Preferred oxidases in the context of the present invention are oxidases classified under EC 1.10.3, which are oxidases capable of catalyzing oxidation of phenolic groups. Oxidases are enzymes employing molecular oxygen as acceptor (i.e. enzymes catalyzing oxidation reactions in which molecular oxygen functions as oxidizing agent).

As already mentioned, laccases (EC 1.10.3.2) are very suitable oxidases in the context of the invention. Examples of other potentially useful, phenol-oxidizing oxidases in the context of the invention include the catechol oxidases (EC 1.10.3.1). The use of mixtures of different phenol-oxidizing oxidases may also be appropriate in some cases.

Laccases are obtainable from a variety of microbial sources, notably bacteria and fungi (including filamentous fungi and yeasts), and suitable examples of laccases are to found among those obtainable from fungi, including laccases obtainable from strains of Aspergillus, Neurospora (e.g. *N. crassa*), Podospora, Botrytis, Coillybia, Fomes, Lentinus, Pleurotus, Trametes [some species/strains of which are known by various names and/or have previously been classified within other genera; e.g. *Trametes villosa=T. pinsitus=*

*Polyporus pinsitis* (also known as *P. pinsitus* or *P. villosus*)= *Coriolus pinsitus*], *Polyporus, Rhizoctonia* (e.g. *R. solani*), Coprinus (e.g. *C. plicatilis*), Psatyrella, Myceliophthora (e.g. *M. thermophila*), Schytalidium, Phlebia (e.g. P. radita; see WO 92/01046), or Coriolus (e.g. *C. hirsutus*; see JP 2-238885).

Preferred laccases in the context of the invention include laccase obtainable from *Trametes villosa* and laccase obtainable from *Myceliophthora thermophila*.

For *Trametes villosa* laccase, the amount of laccase employed in the process of the invention should generally be in the range of 0.01–1000 kLACU per kg (dry weight) of gellable material, preferably 0.05–100 kLACU/kg of gellable material, and will typically be in the range of 0.1–100 kLACU per kg of gellable material (LACU is the unit of laccase activity as defined below; 1 kLACU=1000 LACU).

Determination of Laccase Activity (LACU)

Laccase activity as defined herein is determined on the basis of spectrophotometric measurements of the oxidation of syringaldazin under aerobic conditions. The intensity of the violet colour produced in the oxidation reaction is measured at 530 nm.

The analytical conditions are: 19 $\mu$M syringaldazin, 23.2 mM acetate buffer, pH 5.5, 30° C., reaction time 1 minute, shaking. 1 laccase unit (LACU) is the amount of enzyme that catalyses the conversion of 1 $\mu$M of syringaldazin per minute under these conditions.

For laccases in general, the amount of laccase employed in the process of the invention will generally be in the range of 0.0001–10 mg of laccase (calculated as pure enzyme protein) per gram (dry weight) of gellable material, more usually 0.001–1 mg/g, and will typically be in the range of 0.01–1 mg of laccase per gram of gellable material.

Peroxidases: Peroxidase enzymes (EC 1.11.1) employed in the method of the invention are preferably peroxidases obtainable from plants (e.g. horseradish peroxidase or soy bean peroxidase) or from microorganisms, such as fungi or bacteria. In this respect, some preferred fungi include strains belonging to the subdivision Deuteromycotina, class Hyphomycetes, e.g. Fusarium, Humicola, Tricoderma, Myrothecium, Verticillum, Arthromyces, Caldariomyces, Ulocladium, Embellisia, Cladosporium or Dreschlera, in particular *Fusarium oxysporum* (DSM 2672), *Humicola insolens, Trichoderma resii, Myrothecium verrucana* (IFO 6113), *Verticillum alboatrum, Verticillum dahlie, Arthromyces ramosus* (FERM P-7754), *Caldariomyces fumago, Ulocladium chartarum, Embellisia alli* or *Dreschlera halodes*.

Other preferred fungi include strains belonging to the sub-division Basidiomycotina, class Basidiomycetes, e.g. Coprinus, Phanerochaete, Coriolus or Trametes, in particular *Coprinus cinereus* f. *microsporus* (IFO 8371), *Coprinus macrorhizus, Phanerochaete chrysosporium* (e.g. NA-12) or Trametes versicolor (e.g. PR4 28-A).

Further preferred fungi include strains belonging to the sub-division Zygomycotina, class Mycoraceae, e.g. Rhizopus or Mucor, in particular *Mucor hiemalis*.

Some preferred bacteria include strains of the order Actinomycetales, e.g. *Streptomyces spheroides* (ATTC 23965), *Streptomyces thermoviolaceus* (IFO 12382) or *Streptoverticillum verticillium* ssp. *verticillium*.

Other preferred bacteria include *Bacillus pumilus* (ATCC 12905), *Bacillus stearothermophilus, Rhodobacter sphaeroides, Rhodomonas palustri, Streptococcus lactis, Pseudomonas purrocinia* (ATCC 15958) or *Pseudomonas fluorescens* (NRRL B-11).

Further preferred bacteria include strains belonging to Myxococcus, e.g. *M. virescens*.

Other potential sources of useful particular peroxidases are listed in B. C. Saunders et al., *Peroxidase,* London 1964, pp. 41–43.

As already indicated, preferred peroxidases in the context of the invention include peroxidases classified under EC 1.11.1.7. An example of a suitable peroxidase of this type is a peroxidase obtainable from *Coprinus cinereus.*

When employing a peroxidase in a process according to the invention, an amount thereof in the range of 0.00001–1 mg of peroxidase (calculated as pure enzyme protein) per gram (dry weight) of gellable material will generally be appropriate. The amount employed will often be in the range of 0.0001–0.1 mg/g, such as 0.0001–0.01 mg of peroxidase per gram of gellable material.

Oxidizing agents

The enzyme(s) and oxidizing agent(s) used in the process of the invention should clearly be matched to one another, and it is clearly preferable that the oxidizing agent(s) in question participate(s) only in the oxidative reaction involved in the binding process, and does/do not otherwise have any adverse effect on the substances/materials involved in the process.

Oxidases of the types in question, e.g. laccases, are, among other reasons, well suited in the context of the invention since —as mentioned above—they catalyze oxidation by molecular oxygen. Thus, reactions taking place in vessels open to the atmosphere and involving an oxidase as enzyme will be able to utilize atmospheric oxygen as oxidant; it may, however, be desirable to forcibly aerate the reaction medium with air or another oxygen-containing gas (e.g. oxygen-enriched air or, if appropriate, substantially pure oxygen) during the reaction to ensure an adequate supply of oxygen.

As mentioned above, oxidase-catalyzed (e.g. laccase-catalyzed) oxidation involves oxygen, and the consumption of oxygen in the process of the invention leads to the possibility of exploiting the process in a manner which can be advantageous from the point of view of increasing the shelf-life of, e.g., foodstuffs or medicinal products whose preparation entails the use of an embodiment of the process of the invention in which an oxidase (e.g. a laccase) is employed, since the consumption of oxygen initially present in a sealed foodstuffs package or the like will reduce the possibility of oxidative degradation of the packaged contents.

In the case of peroxidases, hydrogen peroxide is a preferred peroxide (oxidizing agent) in the context of the invention and is normally employed in a concentration (in the reaction medium) in the range of 0.01–500 mM, typically in the range of 0.01–100 mM. For many peroxidases, a suitable concentration range will be from 0.05 to 10 mM, e.g. from 0.05 to 5 mM.

pH in the reaction medium

Depending, inter alia, on the characteristics of the enzyme (s) employed, the pH in the aqueous medium (reaction medium) in which the process of the invention takes place will generally be in the range of 3–10, preferably in the range of 4–9, and often in the range of 4–7.

Temperature in the reaction medium

The choice of temperature for the aqueous medium (reaction medium) in which the process of the invention is to take place will be dependent, inter alia, on the temperature optimum and/or thermal stability of the enzymes employed. For carboxylic ester hydrolases, notably pectinesterases, a temperature in the range of 10–50° C. will normally be appropriate for many pectinesterases of relevance, whilst a temperature in the range of 10–70° C. will be generally be suitable for many oxidases and peroxidases.

Thus, for example, if a pectinesterase is to be added to the reaction medium in question before addition of an oxidase (e.g. a laccase) and/or a peroxidase, it will be possible (and may be advantageous from the point of view of accelerating the overall rate of gelation or increase of viscosity in the medium) to initially maintain the temperature of the reaction medium at a value in the upper end of the normal range for the pectinesterase, and then—when the ester hydrolysis reaction is deemed to be have proceeded to a sufficient extent—to raise the temperature of the medium to a value in the upper end of the normal range for the oxidase and/or peroxidase.

However, in cases where substantially simultaneous addition of, for example, a pectinesterase and an oxidase and/or peroxidase to the reaction medium is employed, it will normally be desirable to limit the temperature in the reaction medium to a value which does not exceed the upper end of the normal range for the pectinesterase.

When, for example, a pectic material (e.g. a beet pectin) is employed as gellable material in the process of the invention, and a combination of a pectinesterase and an oxidase (e.g. a laccase) and/or a peroxidase are employed as enzymes, the process of the invention will generally proceed satisfactorily when the reaction medium is maintained at a temperature in the range from ambient temperature (typically about 25° C.) up to about 45° C.

Applications

As already indicated above, gelled products or products of increased viscosity produced according to the invention have a wide range of applications, e.g. in the food and feed areas, the pharmaceutical and agricultural areas, the personal care/personal hygiene area, and in products for animal pets.

In the food area, for example, the invention is believed to be well suited, inter alia, to the gelling of "diet" preserves, such as jams, marmelades and the like, containing little or no sugar.

A particularly interesting and valuable property of certain gel products ("hydrogels") produced according to the invention is their ability when dried or dehydrated to absorb many times their own weight of liquid (more particularly water or an aqueous medium, e.g. a body fluid such as urine or blood). Materials exhibiting such absorption properties are sometimes referred to as "superabsorbent" materials.

Initially, the most important property in connection with superabsorbent materials was regarded as being the total absorption capacity. Subsequently, however, a number of other properties have been recognized as being of great importance. These properties include the following: rate of absorption; ability to resist so-called gel blocking (whereby part of the absorbing material becomes saturated with liquid and prevents access of further liquid to the remaining part of the absorbing material); and absorption under load (AUL; i.e. the ability of a superabsorbent material to absorb liquid when subjected, e.g., to compression or to centrifugal forces.

Certain products obtainable according to the present invention, e.g. gelled products produced from pectic materials such as sugar beet pectin, appear to be very well suited for use as absorbent materials of the above-outlined type, and the present invention encompasses such use. As examples of applications of the liquid-absorption properties of dried or dehydrated gel products obtainable according to the invention may be mentioned their use as an absorbent in: disposable nappies or diapers for infants or for persons suffering from incontinence; disposable feminine hygiene products (sanitary towels, sanitary napkins, panty protectors, tampons and the like); and disposable materials of the "cat litter" type for domestic and other animals (e.g. cats or rodents) for absorption of urine/faeces therefrom.

Drying or dehydration of gelled products of the type in question may suitably be achieved, for example, by drying them under vacuum at ambient temperature or at a moderately elevated temperature (e.g. a temperature up to about 40° C.). In some cases a pre-treatment such as washing with a water-miscible organic solvent (e.g. acetone, ethanol or the like) may be of value in reducing the water content of a gel prior to final drying by, for example, vacuum treatment.

The environmental and other advantages associated with the use of absorbent materials, such as gelled pectin products prepared in accordance with the invention, which may be prepared straightforwardly and safely from bio-renewable sources, and which themselves are readily biodegradable, will be apparent to a person of ordinary skill in the art.

Further aspects of the present invention relate to:
a gelled product obtained or obtainable by a method according to the invention;
an embodiment of the method according to the invention wherein a gelled product formed thereby is subjected to a drying or dehydration procedure (e.g. as outlined above);
a dried or dehydrated gel product obtained or obtainable (i) by the latter embodiment of the method according to the invention, or (ii) by drying or dehydrating a gelled product according to the invention;
the use of a gelled product of the invention in the manufacture of an absorbent material for absorbing an aqueous medium (e.g. a body fluid, such as urine or blood); and
the use of a dried or dehydrated gel product according to the invention as an absorbent material for absorbing an aqueous medium (e.g. a body fluid as mentioned above).

The present invention is further illustrated by the following examples, which are not in any way intended to limit the scope of the invention as claimed.

EXAMPLE 1

Gelation of Sugar Beet Pectin

The following enzymes were employed in connection with the example below:
pectinesterase (PE; obtained as described in WO 94/25575);
*Trametes villosa* laccase (produced by Novo Nordisk A/S, Bagsvaerd, Denmark);
rhamnogalacturonan-acetylesterase (RGAE; obtained as described in WO 93/20190);
α-arabinofuranosidase (α-ARA; obtainable, e.g., from MEGAZYME, Australia).

Gelation procedure 1200 grams of a 2% w/w aqueous solution of sugar beet pectin was prepared by dissolving 24.0 grams of sugar beet pectin (GENU beta pectin, type BETA, from Hercules Inc.) in 1176 grams of deionized water at 80° C. with vigorous stirring. To the cooled solution (ca. 25° C.) was added an aqueous solution of calcium chloride dihydrate so as to give a content of $Ca^{2+}$ ions corresponding to 1.5% w/w (dry weight) of the amount of pectin, and the pH of the solution was then adjusted to 4.0 by addition of 4M aqueous NaOH solution.

Three 300 g aliquots of the resulting solution were then treated as follows, respectively (giving samples I, II and III, respectively):
Sample I: no enzyme added
Sample II: RGAE added (25 μg enzyme protein/g pectin)
Sample III: α-ARA added (25 μg enzyme protein/g pectin)

After preparation, the three samples were allowed to stand for 30 minutes at 40° C. Each of four 50 gram aliquots of each of the three samples I, II and III was then placed in a 100 ml beaker (beaker A, B, C and D, respectively). The aliquots in the beakers were then treated as follows:

Beaker A: control (no enzyme added)
Beaker B: PE (10 PEU/kg pectin)
Beaker C: laccase (3.5 LACU/g pectin)
Beaker D: PE (10 PEU/kg pectin+laccase (3.5 LACU/g pectin)

The beakers were kept at 45° C. for 30 minutes, during which time the content of each beaker was aerated by bubbling with atmospheric air; the content of each beaker was then divided into two samples. The resulting samples (2×12=24 in all) were kept in a refrigerator for one week, after which their hardness was measured by Texture Analysis (vide supra), using an SMS Texture Analyzer TA-XT2 (Stable Micro Systems; XT.RA Dimensions, Operating Manual version 37) with a flat compression cylinder of diameter 20 mm.

The measurement conditions were as follows:
% gel deformation (compression): 30%
Rate of deformation (compression): 2 mm/sec In the case of samples exhibiting no gel formation (or only weak gel formation), only a visual evaluation was made.

The results obtained are given below (average of two measurements). It should be noted that for simplicity, the peak force for each gel is given here in Newtons (N) rather than $N/m^2$, since the same test probe (having the same cross-sectional cylinder area) was used throughout:

| Sample/beaker No. (treatment) | Force (N) |
|---|---|
| IA (no enzyme treatment) | no gel formation |
| IB (PE) | weak gel formation |
| IC (laccase) | 1.4 |
| ID (PE + laccase) | 3.7 |
| IIA (RGAE) | no gel formation |
| IIB (RGAE + PE) | weak gel formation |
| IIC (RGAE + laccase) | 0.6 |
| IID (RGAE + PE + laccase) | 3.0 |
| IIIA ($\alpha$-ARA) | no gel formation |
| IIIB ($\alpha$-APA + PE) | weak gel formation |
| IIIC ($\alpha$-ARA + laccase) | 0.3 |
| IIID ($\alpha$-ARA + PE + laccase) | 4.3 |

It is apparent from the above results that treatment with PE and laccase gives, in all cases, gels of significantly higher strength (hardness) than those obtained using PE in the absence of laccase, or using laccase in the absence of PE. The results also indicate that treatment of the pectic starting material with certain pectin-debranching enzymes (in this case $\alpha$-ARA) prior to treatment with PE and laccase in combination can result in a further increase in the strength (hardness) of the resulting gel.

In this connection, notably when employing a pectic material as gellable material in the method of the invention, it is contemplated that a treatment with certain other debranching enzymes (or other types of enzymes), e.g. certain types of acetylesterase [other than rhamnogalacturonan-acetylesterase (RGAE)], such as a pectin-acetylesterase or xylan-acetylesterase, or enzymes such as arabinanases or galactanases, may also result in improved properties (such as improved gel strength, or improved liquid-absorption or liquid-retention ability of dried gel products) when performed as, e.g., a pre-treatment prior to performing the method of the invention.

Fluid-absorption and -retention properties of dried, gelled products

The following is illustrative of a suitable procedure for examining the ability of dried forms of, e.g., gelled products according to the present invention to absorb and retain aqueous media:

A gel sample may be washed by allowing it to stand in distilled water for 1–2 hours. Water may be removed by filtration, e.g. on a steel mesh filter. The sample is then suitably rinsed thoroughly with copious amounts of water, washed with acetone and dried in a vacuum drying oven, e.g. at 30° C. overnight.

The thus-dried product is then cut into pieces and comminuted, e.g. in a small laboratory mill (a Retsch Ultra Centrifugal Mill ZM 1000 with ring sieve 6.0 is, for example, generally suitable for this purpose).

The Free Swelling Capacity (FSC; i.e. the liquid uptake per gram of dried gel) and the Retention Capacity (RC; i.e. the liquid retention per gram of dried gel) of the dried gel sample may then be suitably be determined as follows:

FSC: A 0.2 g sample of comminuted dried gel is placed in a fine-mesh nylon "teabag" (3.5×6 cm). The closed "teabag" is then immersed for 2 hours in an aqueous medium of interest, e.g. an aqueous solution simulating human urine and having the following composition:

60 mM KCl, 130 mM NaCl, 3.5 mM $MgCl_2 \times 6H_2O$, 2.0 mM $CaCl_2 \times 2H_2O$, 300 mM urea, surface tension adjusted to 60 dynes/cm by addition of Triton™ X-100 (Rohm & Haas) [surface tension measurements may, e.g., be made with a CAHN Dynamic Contact Angle Analyzer (Cahn Instrument Inc.) using the Wilhelmy plate technique].

The soaked "teabag" with contents is allowed to drip-dry for 2 minutes. The FSC for the gel in question is then calculated by dividing the weight (in grams) of liquid absorbed by the gel sample in the teabag by the initial weight (in this case 0.2 g) of the dry gel sample.

RC: The drip-dried "teabag" is centrifuged (using, for example, a WIFUG laboratory centrifuge 500E running at 327 x g for 10 minutes). RC for the gel in question is then calculated by dividing the weight (in grams) of absorbed liquid remaining in the teabag after centrifugation by the initial weight (in this case 0.2 g) of the dry gel sample.

EXAMPLE 2

Swelling and Retention Capacities of Gels

The following enzymes were employed in connection with the example below.

pectinesterase (PE; obtained as described in WO 94/25575); *Myceliophthera thermophila* laccase (produced by Novo Nordisk A/S, Bagsvaerd, Denmark).

Portions of 3% (w/v) aqueous solutions of sugar beet pectin were prepared by dissolving 3.0 g of sugar beet pectin (GENU beta pectin, type BETA, from Hercules Inc.) in 100 ml of hot (ca. 80° C.) deionized water with vigorous stirring. The pH was not adjusted. After cooling to room temperature (ca. 25° C.), the solutions were incubated at that temperature with different amounts of PE for two hours. Laccase (0.6 mg/g of pectin) was then added to each solution, and the solutions were then incubated at room temperature for a further two hours.

The FSC and RC for the gels were then determined using the procedure described above.

The results obtained are given below

| Amount of PE (PEU/kg of pectin) | FSC (g/g) | RC (g/g) |
|---|---|---|
| 0 | 10.5 | 6.4 |
| 13.3 | 16.5 | 9.5 |
| 25.9 | 15.6 | 8.5 |
| 51.7 | 17.6 | 10.8 |

These results show clearly that treatment with PE prior to the treatment with laccase results in a marked improvement in the liquid-absorption (swelling) and liquid-retention properties of the gels.

We claim:

1. A method for causing gelling or increase of viscosity of an aqueous medium containing a pectic material which has functionalities with phenolic hydroxy groups; the method comprising treating said aqueous medium with:
   (i) a carboxylic ester hydrolase (EC 3.1.1); and
   (ii) an oxidase (EC 1.10.3) and/or a peroxidase (EC 1.11.1) in the presence of an oxidizing agent suitable for use with said oxidase and/or peroxidase.

2. The method according to claim 1, wherein said pectic material is a material obtainable from a member of the plant family Chenopodiaceae.

3. The method according to claim 1, wherein said pectic material is obtainable from sugar beets.

4. The method according to claim 1, wherein said pectic material is extracted from sugar beet pulp.

5. The method according to claim 1, wherein said treatment of said aqueous medium is preceded by a treatment with an α-arabinofuranosidase.

6. The method according to claim 1, wherein said treatment of said aqueous medium is preceded by a treatment with an acetylesterase.

7. The method according to claim 1, wherein said carboxylic ester hydrolase is a pectinesterase (EC 3.1.1.11).

8. The method according to claim 1, wherein said oxidase is a laccase (EC 1.10.3.2).

9. The method according to claim 1, wherein said peroxidase is a peroxidase classified under EC 1.11.1.7.

10. The method according to claim 1, wherein the gelled product formed is subjected to a drying or dehydration procedure.

11. A gelled product obtainable by a method according to claim 1.

12. A dried or dehydrated gel product obtainable by a method according to claim 10.

13. A method for preparing an absorbent material, said method comprising:
   (a) treating a pectic material with:
      (i) a carboxylic ester hydrolase (EC 3.1.1) and
      (ii) an oxidase (EC 1.10.3) and/or a peroxidase (EC 1.11.1) in the presence of an oxidizing agent suitable for use with said oxidase and/or peroxidase; and
   (b) subjecting said treated material to dehydration.

14. An absorbent material prepared using a method as defined in claim 13.

15. A method for increasing the shelf-life of a packaged pectic material, said method comprising:
   (a) treating said material with:
      (i) a carboxylic ester hydrolase (EC 3.1.1); and
      (ii) an oxidase (EC 1.10.3) in the presence of an oxidizing agent suitable for use with said oxidase; and
   (b) sealing said treated material in an airtight container.

16. A packaged material prepared using a method as defined in claim 15.

* * * * *